United States Patent [19]
Barclay et al.

[11] Patent Number: 5,395,336
[45] Date of Patent: Mar. 7, 1995

[54] METHOD FOR JOINING PORTIONS OF A INFLATION/EXPANSION CATHETER AND A CATHETER SO FORMED

[75] Inventors: Anita L. Barclay, Clute; Robert Lobdell, Angleton, both of Tex.

[73] Assignee: Mallinckrodt Medical, Inc., St. Louis, Mo.

[21] Appl. No.: 52,354

[22] Filed: Apr. 26, 1993

[51] Int. Cl.[6] ............................................. A61M 29/00
[52] U.S. Cl. .................................... 604/103; 606/194; 156/158
[58] Field of Search ................... 604/96, 103, 280; 606/192, 194; 156/83, 86, 158, 294, 296, 304.2, 304.6

[56] References Cited

U.S. PATENT DOCUMENTS

| | | | |
|---|---|---|---|
| 3,528,869 | 9/1970 | Dereniuk | 156/294 |
| 3,972,548 | 8/1976 | Roseen | 156/158 X |
| 4,092,193 | 5/1978 | Brooks | 156/158 X |
| 4,636,272 | 1/1987 | Riggs | 156/158 |
| 4,684,363 | 8/1987 | Ari et al. | 606/192 X |
| 4,775,371 | 10/1988 | Mueller, Jr. | 604/98 X |
| 4,781,681 | 11/1988 | Sharrow et al. | 604/103 X |
| 4,782,834 | 11/1988 | Maguire et al. | 606/194 X |
| 4,838,881 | 6/1989 | Bennett | 156/294 X |
| 4,913,701 | 4/1990 | Tower | 604/103 |
| 4,954,678 | 9/1990 | Harmony et al. | 156/274.4 X |
| 5,098,381 | 3/1992 | Schneider | 604/96 |
| 5,135,487 | 8/1992 | Morrill et al. | 604/96 |
| 5,137,591 | 8/1992 | Gansbuehler et al. | 156/86 |
| 5,154,725 | 10/1992 | Leopold | 604/96 X |
| 5,160,396 | 11/1992 | Jensen et al. | 156/304.2 |
| 5,160,559 | 11/1992 | Scovil et al. | 156/304.2 |
| 5,209,729 | 5/1993 | Hofmann et al. | 604/96 |

Primary Examiner—C. Fred Rosenbaum
Assistant Examiner—Frank Wilkens
Attorney, Agent, or Firm—David A. Hey

[57] ABSTRACT

The present invention relates to a method of joining portions of an inflation/expansion catheter. In particular, the present invention relates to an improved method of joining coaxial lumen portions to multi-lumen portions of an inflation/expansion catheter. More particularly, the present invention relates to a method of joining a multi-lumen shaft to a coaxial balloon shaft of a dilatation catheter.

6 Claims, 3 Drawing Sheets

METHOD FOR JOINING PORTIONS OF A INFLATION/EXPANSION CATHETER AND A CATHETER SO FORMED

BACKGROUND

The present invention relates to a method of joining portions of an inflation/expansion catheter. In particular, the present invention relates to an improved method of joining coaxial lumen portions to multi-lumen portions of an inflation/expansion catheter. Further, the present invention relates to a dilatation catheter formed by such method.

Percutaneous transluminal angioplasty (PTA) procedures typically are performed by introducing a dilatation balloon catheter into the cardiovascular system of the patient through the brachial or femoral arteries via a sheath introducer. In particular, a guidewire and the dilatation balloon catheter are introduced through the sheath introducer, the guidewire being disposed within an inner lumen of the balloon catheter. The guidewire and balloon are advanced until the dilatation balloon is properly located within the area of lesion to be treated. Once positioned, the dilatation balloon is pressure inflated to a predetermined size using a radiopaque liquid, such as contrast medium, through a second lumen of the balloon catheter, in order to radially compress the atherosclerotic plaque of the lesion against the inside of the artery wall and thereby dilate the lumen of the artery. The dilatation balloon is then deflated. Inflation and deflation of the balloon may be repeated several times within the lesion until the desired results are achieved. The balloon catheter is then removed so that blood flow may be resumed through the dilated artery.

It is desirable to provide a method of joining coaxial lumen and multi-lumen portions of a dilatation catheter so as to maintain the inside diameters of the catheter lumens to as great an extent as possible.

OBJECTS OF THE INVENTION

It is one object of the present invention to provide an improved method of joining portions of an inflation/expansion catheter.

It is another object of the present invention to provide an improved method of joining portions of a dilatation catheter.

SUMMARY OF THE INVENTION

The objects of the present invention are accomplished by the method of joining portions of an inflation/expansion catheter as described in more detail below. In particular, the objects of the present invention will be described in relation to a dilatation catheter as shown in the drawing figures.

DETAILED DESCRIPTION OF THE INVENTION

Figure 1:
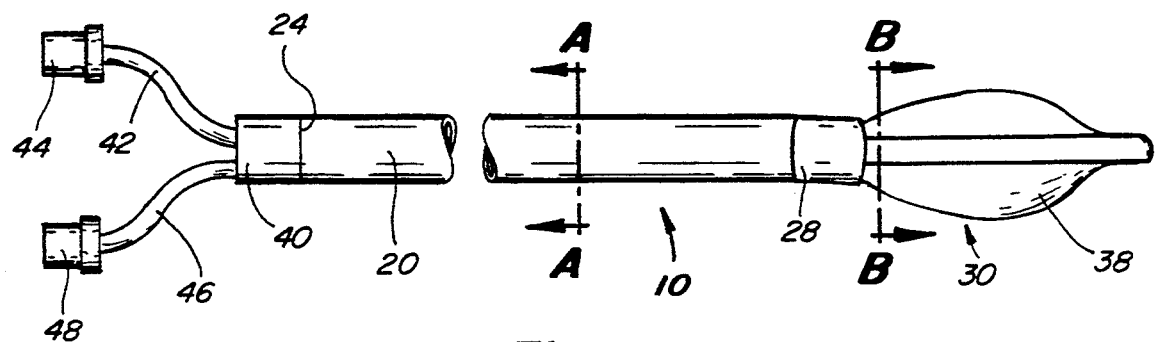
FIG. 1 is a plan view of a dilatation catheter according to a first embodiment of the present invention.

FIG. 1 is a plan view of a dilatation catheter according to a first embodiment of the present invention. The catheter, generally designated by reference numeral 10, includes a multi-lumen shaft 20, one lumen of which serves as a guidewire lumen, and the other lumen of which serves as a balloon inflation lumen. The multi-lumen shaft 20, is joined at connection portion 40, to two connection lumens 42, 46. The connection lumen 42, is connected to the guidewire lumen of the multi-lumen shaft 20, at the connection portion 40, and includes a hub connector 44, at the proximal end thereof. The connection lumen 46, is connected to the inflation lumen of the multi-lumen shaft 20, at the connection portion 40, and includes a hub connector 48, at the proximal end thereof.

Figure 2:
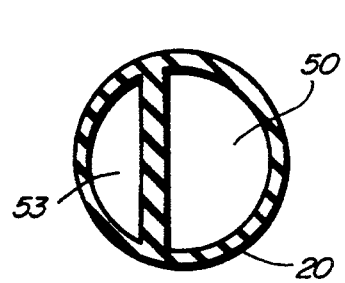
FIG. 2 is a cross-sectional view of dilatation catheter according to the present invention, taken along line A—A of FIG. 1.
Figure 3:
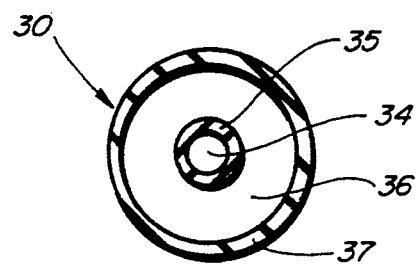
FIG. 3 is a cross-sectional view of a dilatation catheter according to the present invention, taken along line B—B of FIG. 1.

The guidewire lumen runs the entire length of the multi-lumen shaft 20, from a proximal end 24, to a joining portion 28. The inflation lumen also runs from the proximal end 24, of the multi-lumen shaft 20, to the joining portion 28. As shown most clearly in FIG. 2, the guidewire lumen 50, and inflation lumen 53, are in a side-by-side configuration. As clearly shown, the guidewire lumen 50, has a much larger cross-sectional area than that of the inflation lumen 53. The multi-lumen shaft 20, is connected to a balloon shaft generally designated by reference numeral 30, at the joining portion 28. As best shown in FIG. 3, balloon shaft 30, comprises two separate tubes arranged in a coaxial configuration. In particular, the balloon shaft 30, includes an inner member 35, having a guidewire lumen 34; and a balloon member 37, having an inflation lumen 36. The multi-lumen shaft 20, is connected to the balloon shaft 30, in such a manner that the guidewire lumen 50, of the multi-lumen shaft 20, and the guidewire lumen 34, of the inner member 35, form a continuous lumen running the entire length of the catheter 10; and the inflation lumen 53, of the multi-lumen shaft 20, and the inflation lumen 36, of balloon member 37, form a continuous lumen running from the proximal end of the catheter 10, to a balloon 38, formed along a portion of the balloon member 37. The method of the present invention for connecting the multi-lumen shaft 20, and the balloon shaft 30, is described in greater detail below.

The method of joining the multi-lumen shaft 20, and balloon shaft 30, according to the present invention comprises the following steps. Initially, the multi-lumen shaft 20, is cut to length. Tables 1 and 2 show appropriate lengths for the multi-lumen shaft 20, of varying dilatation balloon sizes. The cut on the distal end of the multi-lumen shaft 20, may be a diagonal cut to facilitate the attachment of the multi-lumen shaft 20, to the balloon shaft 30. Following cutting, the multi-lumen shaft 20, should be thoroughly cleaned on the outside with a lint-free wipe and freon, and on the inside by attachment to a compressed air source.

Figure 4:
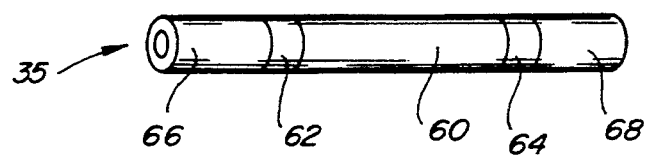
FIG. 4 is a plan view of the inner member of the balloon shaft of the dilatation catheter according to the present invention.

FIG. 4 is a plan view of the inner member 35, of the balloon shaft 30, according to the present invention. In particular, FIG. 4 shows placement of marker bands, preferably gold marker bands, 62, 64, on the inner member 35, of the balloon shaft 30. Tables 1 and 2 include lengths for the marker band section 60, of the inner member 35, i.e. measured form the outside of marker band 62, to the outside of marker band 64.

An inner member 35, prefitted with marker bands 62, 64, is cut to length according to the dimensions given in Tables 1 and 2. The inner member proximal shaft side 66, is measured from the outside of marker band 62, and the inner member distal shaft side 68, is measured from the outside of marker band 64. Following cutting, the inner member 35, should be thoroughly cleaned with a lint-free wipe and if necessary, degreased; for example, by using freon.

Two or three small mandrils, typical sizes of which are shown in Tables 1 and 2, are then inserted through the entire length of inflation lumen 53, of the multi-lumen shaft 20, such that a portion of the mandrils extend beyond each end of the multi-lumen shaft 20. The mandrils should extend 1 to 2 cm beyond the distal end of the multi-lumen shaft 20, to facilitate further processing. The sizes of the small mandrils should be chosen so as to ensure a snug fit between the mandrils and the inside diameter of the inflation lumen 53. Optionally, a pin gauge may be used to enlarge the guidewire lumen 50, of the multi-lumen shaft 20, to a distance of about 1 cm.

The inner member 35, of balloon shaft 30, is slidingly engaged over an appropriately sized mandril; e.g. 0.021", and is threaded over the mandril such that the mandril extends beyond both ends of the inner member 35. The inner member mandril is then inserted approximately 8 to 10 cm into the guidewire lumen 50, of the multi-lumen shaft 20. The inner member 35, is then threaded along the inner member mandril and the proximal shaft side 66, of the inner member 35, is inserted about 1 cm into the guidewire lumen 50, of the multi-lumen shaft 20.

Figure 5:
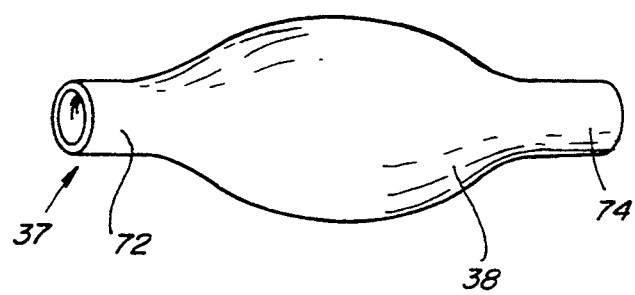
FIG. 5 is a plan view of the balloon member of the balloon shaft of the dilatation catheter according to the present invention.

The balloon member 37, of balloon shaft 30, has a length in accordance with the dimensions shown in Tables 3 and 4. As best shown in FIG. 5, the overall length of balloon member 37, is determined by addition of the dimensions shown in Tables 3 and 4 for balloon 38, size; proximal shaft 72, length; and distal shaft 74, length. The balloon member 37, is slidingly engaged over the inner member mandril and the inner member 35, and is threaded over the mandril and the inner member 35, toward the distal end of the multi-lumen shaft 20. The balloon member 37, is then slidingly engaged over the two or three mandrils inserted into the inflation lumen 53, of multi-lumen shaft 20, and then over the distal end of the multi-lumen shaft 20, to create a lap joint of about 1 cm in length. The balloon member 37, may optionally include an adaptation expansion at the proximal end, so as to facilitate the engagement of the balloon member 37, over the multi-lumen shaft 20, and the creation of the lap joint.

A teflon tube, having the size indicated in Tables 3 and 4 is engaged over the multi-lumen shaft 20, and positioned to cover the lap joint. The teflon tube may include a short transverse slit at the distal end, to facilitate the positioning of the teflon tube over the lap joint. A first glass capillary tube having the inside diameter shown in Tables 3 and 4 is then engaged over the multi-lumen shaft 20, and positioned to cover the teflon tube.

Various methods may be used to accomplish a good seal or bond between the multi-lumen shaft 20, and the balloon shaft 30, at the lap joint.

According to one method, when the teflon and glass capillary tubes are in place, the lap joint portion is placed in a heater block assembly set at a temperature and air flow indicated in Tables 3 and 4. The lap joint is positioned to be in the middle of the air flow nozzle and is rotated to achieve even heating. The lap joint is heated until it turns a white or milkish color. Care should be taken to heat both edges of the lap joint. Pressure should be applied to the lap joint during heating and subsequent cooling in air.

Following the heating and cooling steps, the glass capillary and teflon tubes are removed. The lap joint should be smooth and sealed. If not properly sealed, the heating and cooling steps should be repeated using the small second glass capillary tube indicated in Tables 3 and 4. When the lap joint is sealed properly, the mandrils may all be removed.

In a preferred method, the lap joint portion covered by the teflon and glass capillary tubes is placed in a heater coil and compression monitor assembly set at predetermined values for control of current and time. In particular, amps for the heater coil and compression force for the compression monitor may be set in accordance with the parameters indicated in Table 5. The lap joint then cycles through a heating time, compression time, and cooling time, also as indicated in Table 5.

Following the heating, compression and cooling steps, the glass capillary and teflon tubes are removed. The lap joint should be smooth and sealed. If not properly sealed, the heating, compression and cooling steps may be repeated using the small second glass capillary tube indicated in Tables 3 and 4. When the lap joint is sealed properly, the mandrils may all be removed.

The provision of a diagonal cut on the multi-lumen shaft 20, provides several advantages in the above process. In particular, as noted above, the diagonal cut facilitates the attachment of the multi-lumen shaft 20, to the inner member 35, and the balloon member 37, of the balloon shaft 30. In addition, the diagonal cut reduces the amount of material which undergoes the sealing or bonding process. In particular, the amount of material located in the lap joint area is reduced, thereby making the bonding of the multi-lumen shaft 20, to the various components of the balloon shaft 30, easier to control and providing a more even and smooth bond area.

TABLE 1

| Baloon Size (mm × cm) | Multi-Lumen (± 0.5 cm) | Marker Band Length (± 0.5 mm) | Mandril O.D. (inches) (± 0.002") | Inner Member Proximal Shaft Side (± 0.2 cm) | Inner Member Distal Shaft Side (± 0.2 cm) | Inner Member Lumen Size |
| --- | --- | --- | --- | --- | --- | --- |
| 2.0 × 2.0 | 109 cm | 1.4 cm | .011 & .011 | 8.6 | 2.8* | .025 × .045 |
| 2.0 × 4.0 | 109 cm | 3.4 cm | .011 & .011 | 8.6 | 2.8* | .025 × .045 |
| 2.5 × 2.0 | 109 cm | 1.4 cm | .011 & .011 | 8.6 | 2.8* | .025 × .045 |
| 2.5 × 4.0 | 109 cm | 3.4 cm | .011 & .011 | 8.6 | 2.8* | .025 × .045 |
| 3.0 × 2.0 | 109 cm | 1.4 cm | .011 & .011 | 8.6 | 2.8* | .025 × .045 |
| 3.0 × 4.0 | 109 cm | 3.4 cm | .011 & .011 | 8.6 | 2.8* | .025 × .045 |
| 3.5 × 2.0 | 109 cm | 1.4 cm | .011 & .011 | 8.6 | 2.8* | .025 × .045 |

TABLE 1-continued

| Baloon Size (mm × cm) | Multi-Lumen (± 0.5 cm) | Marker Band Length (± 0.5 mm) | Mandril O.D. (inches) (± 0.002") | Inner Member Proximal Shaft Side (± 0.2 cm) | Inner Member Distal Shaft Side (± 0.2 cm) | Inner Member Lumen Size |
|---|---|---|---|---|---|---|
| 3.5 × 4.0 | 109 cm | 3.4 cm | .011 & .011 | 8.6 | 2.8* | .025 × .045 |

*Make sure inner member is 1 cm ± 0.5 cm shorter than the Distal Shaft Length (Tables 3 and 4). Make adjustments if necessary.
2.0 × 2.0 through 3.5 × 4.0; mandril length 125 cm ± 5 cm. Make sure each end is rounded off on both mandrils before using.

TABLE 2

| Baloon Size (mm × cm) | Multi-Lumen (± 0.5 cm) | Marker Band Length (± 0.5 mm) | Mandril O.D. (inches) (± 0.002") | Inner Member Proximal Shaft Side (± 0.2 cm) | Inner Member Distal Shaft Side (± 0.2 cm) | Inner Member Lumen Size |
|---|---|---|---|---|---|---|
| 4.0 × 2.0 | 77 cm | 1.4 cm | .012 & .012 | ** | Long*** | .025 × .045 |
| 4.0 × 4.0 | 77 cm | 3.4 cm | .012 & .012 | ** | Long*** | .025 × .045 |
| 5.0 × 2.0 | 77 cm | 1.4 cm | .012 & .012 | ** | Long*** | .025 × .045 |
| 5.0 × 4.0 | 77 cm | 3.4 cm | .012 & .012 | ** | Long*** | .025 × .045 |
| 6.0 × 2.0 | 77 cm | 1.4 cm | .012 & .012 | ** | Long*** | .025 × .045 |
| 6.0 × 4.0 | 77 cm | 3.4 cm | .012 & .012 | ** | Long*** | .025 × .045 |
| 7.0 × 2.0 | 77 cm | 1.4 cm | .012 & .012 | ** | Long*** | .025 × .045 |
| 7.0 × 4.0 | 77 cm | 3.4 cm | .012 & .012 | ** | Long*** | .025 × .045 |
| 8.0 × 3.0 | 77 cm | 2.4 cm | .012 & .012 | ** | Long*** | .025 × .045 |

**Cut inner member to fit balloon.
***Cut inner member even with Distal Shaft Length (Tables 3 and 4) after adaption is completed.
4.0 × 2.0 through 8.0 × 3.0; mandril length 90 cm ± 5 cm. Make sure each end is rounded off on both mandrils before using.

TABLE 3

| Balloon Size (mm × cm) | Proximal Shaft Length (± 2 mm) | Distal Shaft Length (± 0.2 cm) | Teflon Size (± 0.001") | 1st Glass I.D. (± .2 cm) | 2nd Glass I.D. (± .2 cm) | Temperature (± 10 F.) | Nozzle Air Flow (SCFH) |
|---|---|---|---|---|---|---|---|
| 2.0 × 2.0 | 7 cm | 3 cm | 0.052 | .063/.064 | .060/.061 | 250 | 20–30 |
| 2.0 × 4.0 | 7 cm | 3 cm | 0.052 | .063/.064 | .060/.061 | 250 | 30–40 |
| 2.5 × 2.0 | 7 cm | 3 cm | 0.052 | .063/.064 | .060/.061 | 270 | 30–40 |
| 2.5 × 4.0 | 7 cm | 3 cm | 0.052 | .063/.064 | .060/.061 | 270 | 30–40 |
| 3.0 × 2.0 | 7 cm | 3 cm | 0.052 | .064/.065 | .062/.063 | 270 | 30–40 |
| 3.0 × 4.0 | 7 cm | 3 cm | 0.052 | .064/.065 | .062/.063 | 270 | 30–40 |
| 3.5 × 2.0 | 7 cm | 3 cm | 0.052 | .064/.065 | .062/.063 | 270 | 30–40 |
| 3.5 × 4.0 | 7 cm | 3 cm | 0.052 | .064/.065 | .062/.063 | 270 | 30–40 |

Length of teflon is 5 cm ± 5 mm.
Check temperature with probe to ensure proper temperature.

TABLE 4

| Balloon Size (mm × cm) | Proximal Shaft Length (± 2 mm) | Distal Shaft Length (± 0.2 cm) | Teflon Size (± 0.001") | 1st Glass I.D. (± .2 cm) | 2nd Glass I.D. (± .2 cm) | Temperature (± 10 F.) | Nozzle Air Flow (SCFH) |
|---|---|---|---|---|---|---|---|
| 4.0 × 2.0 | 7 cm | 2 cm | 0.052 | .066/.067 | .065/.066 | 280 | 30–40 |
| 4.0 × 4.0 | 7 cm | 2 cm | 0.052 | .066/.067 | .065/.066 | 280 | 30–40 |
| 5.0 × 2.0 | 7 cm | 2 cm | 0.052 | .067/.068 | .065/.066 | 280 | 30–40 |
| 5.0 × 4.0 | 7 cm | 2 cm | 0.052 | .067/.068 | .065/.066 | 280 | 30–40 |
| 6.0 × 2.0 | 7 cm | 2 cm | 0.052 | .067/.068 | .065/.066 | 290 | 30–40 |
| 6.0 × 4.0 | 7 cm | 2 cm | 0.052 | .067/.068 | .065/.066 | 290 | 30–40 |
| 7.0 × 2.0 | 7 cm | 2 cm | 0.052 | .067/.068 | .065/.066 | 290 | 30–40 |
| 7.0 × 4.0 | 7 cm | 2 cm | 0.052 | .067/.068 | .065/.066 | 290 | 30–40 |
| 8.0 × 3.0 | 7 cm | 2 cm | 0.052 | .068/.069 | .066/.067 | 290 | 30–40 |

Length of teflon is 5 cm ± 5 mm.
Check temperature with probe to ensure proper temperature.

TABLE 5

| Balloon Size (mm × cm) | Amps | Compression Force (Lbs) | Heating Time (Seconds) | Compression Time (Seconds) | Cooling Time (Seconds) |
|---|---|---|---|---|---|
| 2.0 × 2.0 | 6.30 ± .15 | .35 ± .15 | 26.0 ± .6 | 14.0 ± .6 | 10 |
| 2.0 × 4.0 | 6.30 ± .15 | .35 ± .15 | 26.0 ± .6 | 14.0 ± .6 | 10 |
| 2.5 × 2.0 | 6.30 ± .15 | .35 ± .15 | 26.0 ± .6 | 14.0 ± .6 | 10 |
| 2.5 × 4.0 | 6.30 ± .15 | .35 ± .15 | 26.0 ± .6 | 14.0 ± .6 | 10 |
| 3.0 × 2.0 | 6.10 ± .10 | .40 ± .10 | 24.0 ± .4 | 14.0 ± .4 | 10 |
| 3.0 × 4.0 | 6.10 ± .10 | .40 ± .10 | 24.0 ± .4 | 14.0 ± .4 | 10 |
| 3.5 × 2.0 | 6.10 ± .10 | .40 ± .10 | 24.0 ± .4 | 14.0 ± .4 | 10 |
| 3.5 × 4.0 | 6.10 ± .10 | .40 ± .10 | 24.0 ± .4 | 14.0 ± .4 | 10 |
| 4.0 × 2.0 | 6.10 ± .10 | .40 ± .10 | 24.0 ± .4 | 14.0 ± .4 | 10 |

TABLE 5-continued

| Balloon Size (mm × cm) | Amps | Compression Force (Lbs) | Heating Time (Seconds) | Compression Time (Seconds) | Cooling Time (Seconds) |
| --- | --- | --- | --- | --- | --- |
| 4.0 × 4.0 | 6.10 ± .10 | .40 ± .10 | 24.0 ± .4 | 14.0 ± .4 | 10 |
| 5.0 × 2.0 | 6.10 ± .10 | .40 ± .10 | 24.0 ± .4 | 14.0 ± .4 | 10 |
| 5.0 × 4.0 | 6.10 ± .10 | .40 ± .10 | 24.0 ± .4 | 14.0 ± .4 | 10 |
| 6.0 × 2.0 | 6.10 ± .05 | .45 ± .15 | 26.0 ± .6 | 16.0 ± .6 | 10 |
| 6.0 × 4.0 | 6.15 ± .10 | .45 ± .15 | 26.0 ± .6 | 16.0 ± .6 | 10 |
| 7.0 × 2.0 | 6.10 ± .10 | .40 ± .10 | 24.0 ± .4 | 14.0 ± .4 | 10 |
| 7.0 × 4.0 | 6.10 ± .10 | .40 ± .10 | 24.0 ± .4 | 14.0 ± .4 | 10 |
| 8.0 × 3.0 | 6.10 ± .10 | .40 ± .10 | 24.0 ± .4 | 14.0 ± .4 | 10 |

By using the method according to the present invention, it is possible to securely and accurately join different portions of a dilatation catheter. In particular, the method of the present invention makes it possible to join a multi-lumen shaft to a coaxial shaft.

The method described above relating to a two lumen catheter may easily be extended to a catheter having any number of lumens.

Catheters having more than two lumens may be constructed in a very similar method to that described above for catheter 10. It will be easily recognized that the only differences will be the addition of further mandrils and the additional steps of connecting a third set of lumens at the joining portion 28.

Figure 6A:
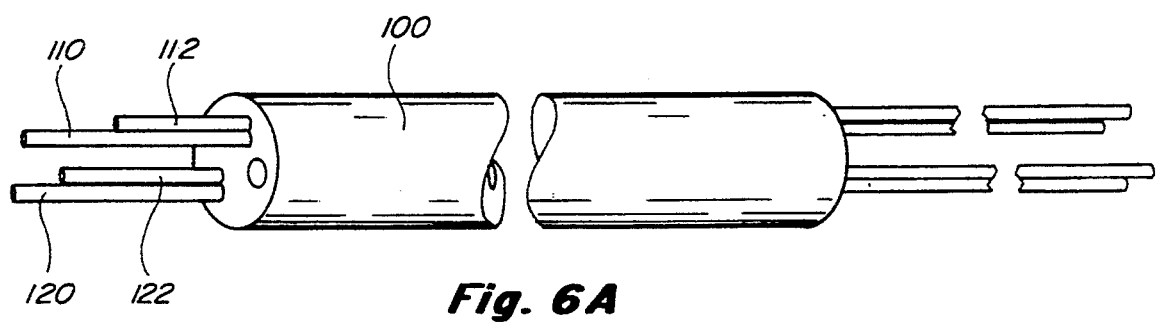
FIG. 6A to 6H show various stages in the production method of the catheter according to one embodiment of the present invention.

FIG. 6A to 6H show the steps in the method according to one embodiment of the present invention. In particular, FIG. 6A shows a multi-lumen shaft 100, having three lumens, wherein a first lumen has mandrils 110 and 112, inserted therethrough, a second lumen has mandrils 120 and 122, inserted therethrough, and a third lumen remains open.

Figure 6B:
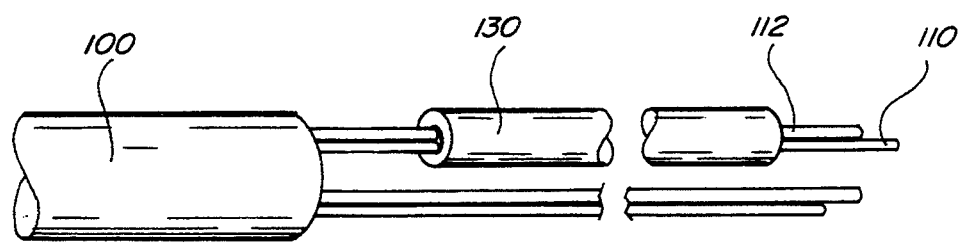

FIG. 6B shows the distal end of the multi-lumen shaft 100, as shown in FIG. 6A, and shows a first proximal shaft 130, engaged over mandrils 110 and 112.

Figure 6C:
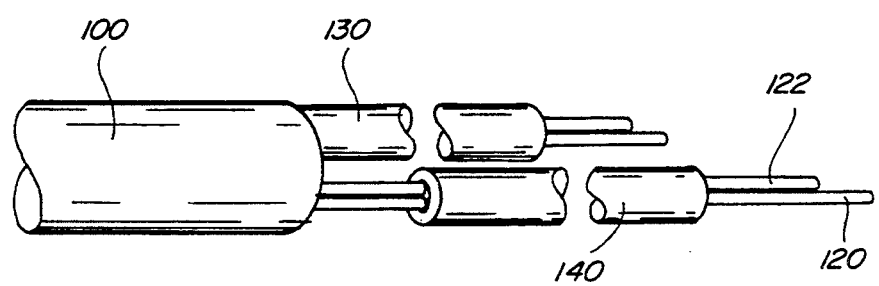
Figure 6D:
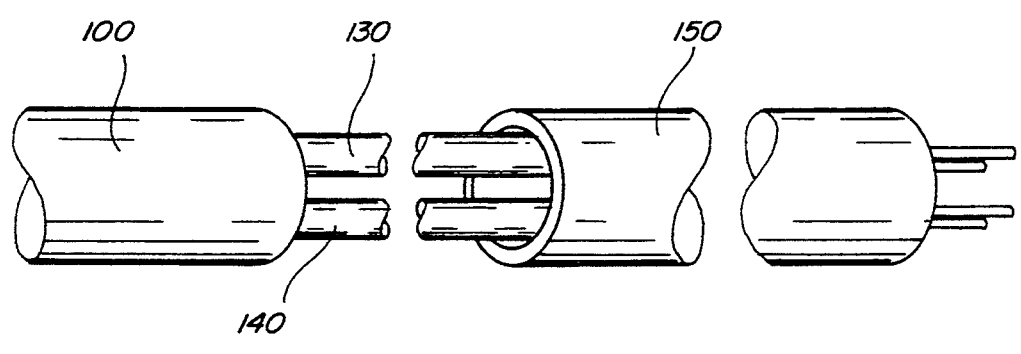

FIG. 6C shows the distal end of the multi-lumen shaft 100, as shown in FIG. 6A, and shows the first proximal shaft 130, attached to the multi-lumen shaft 100, and a second proximal shaft 140, engaged over mandrils 120 and 122.

FIG. 6O shows the distal end of the multi-lumen shaft 100, as shown in FIG. 6A, and shows the first proximal shaft 130, attached to the multi-lumen shaft 100, and the second proximal shaft 140, attached to the multi-lumen shaft 100, and a third proximal shaft 150, engaged over mandrils the first proximal shaft 130, and the second proximal shaft 140.

Figure 6E:
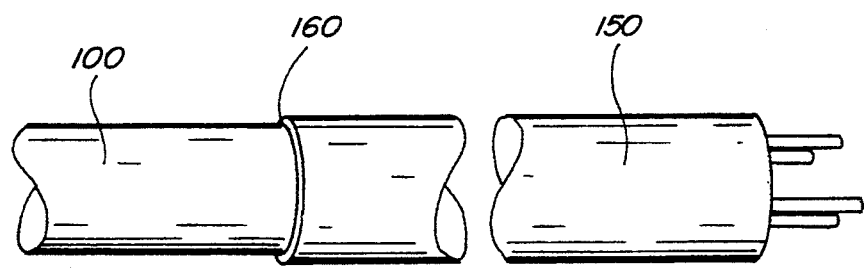

FIG. 6E shows the third proximal shaft 150, attached to the multi-lumen shaft 100, to form a lap joint 160.

Figure 6F:
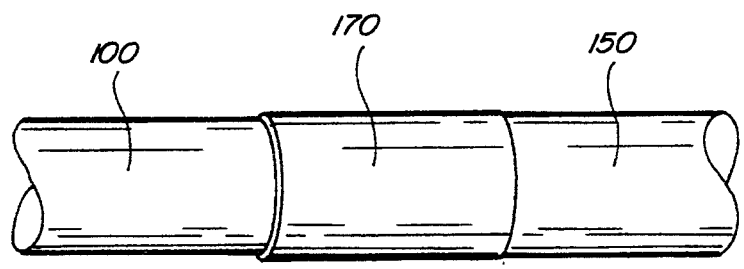

FIG. 6F shows the attached multi-lumen shaft 100, and third proximal shaft 150, having a teflon tube 170, engaged over the lap joint.

Figure 6G:
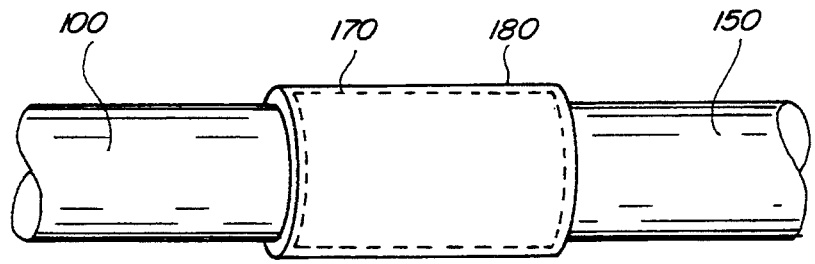

FIG. 6G shows the attached multi-lumen shaft 100, and third proximal shaft 150, having a glass tube 180, engaged over the teflon tube 170.

Figure 6H:
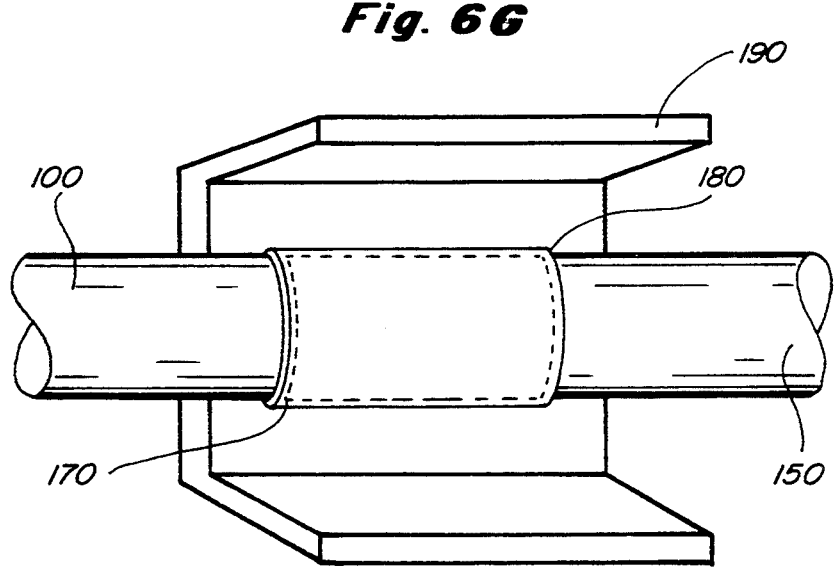

FIG. 6H shows the attached multi-lumen shaft 100, and third proximal shaft 150, having engaged glass tube 180, and teflon tube 170, placed is a treatment assembly 190, for treatment.

In addition, while the above description relates specifically to a dilatation catheter, the method described could easily be used for joining separate portions of almost any type of catheter. For example, the catheter joined by the method according to the present invention may include a lumen for use in the delivery of drugs or other pharmacologic agents.

The foregoing has been a description of certain preferred embodiments of the present invention, but is not intended to limit the invention in any way. Rather, many modifications, variations and changes in details may be made within the scope of the present invention.

What is claimed is:

1. A method of joining portions of a catheter, said catheter including
a proximal shaft with at least two lumens, wherein said at least two lumens are in a side-by-side arrangement;
a distal shaft with at least two members, wherein said at least two tube members are arranged in a coaxial arrangement;
said method comprising the steps of:
a) providing said proximal shaft;
b) inserting at least two mandrils through the entire length of an omen lumen of said proximal shaft such that a portion of said mandrils extends beyond each end of said proximal shaft;
c) providing a tube member of said distal shaft;
d) slidingly engaging one tube member of said distal shaft over said mandrils such that a portion of said mandrils extends beyond each end of said tube member;
e) threading said tube member over said mandrils and inserting a proximal end of said tube member into a distal end of said lumen of said proximal shaft through which said mandrils have been inserted;
f) repeating said stems b, c, d, and e, until only one tube member remains for said distal shaft and only one omen lumen remains for said proximal shaft;
g) slidingly engaging the one remaining tube member over all said mandrils and all previously engaged tube members;
h) threading said remaining tube member over said mandrils and said tube members and slidingly engaging said remaining tube member over the distal end of said proximal shaft to create a lap joint; and
i) treating said lap joint to seal said proximal shaft to said distal shaft.

2. A method according to claim 1, wherein said steps b, c, d, and e form a continuous guidewire lumen; and wherein said steps g, and h form a continuous inflation lumen connected with an inflation/expansion member formed along a portion of the length of said remaining tube member.

3. A method according to claim 1, wherein said steps b, c, d, and e form a continuous delivery lumen; and wherein said steps g, and h form a continuous inflation lumen connected with an inflation/expansion member formed along a portion of the length of said remaining tube member.

4. A method according to claim 1, wherein said step of treating said lap joint comprises:
positioning a teflon tube over the lap joint;

positioning a glass capillary tube over the teflon tube to form an assembly;

placing said assembly within a heater block having an air flow nozzle, such that lap joint is positioned to be in the middle of the air flow nozzle;

rotating said assembly to achieve even heating of said lap joint;

cooling said assembly; and removing said glass capillary tube and said teflon tube.

5. A method according to claim 1, wherein said step of treating said lap joint comprises:

positioning a teflon tube over the lap joint;

positioning a glass capillary tube over the teflon tube to form an assembly;

placing said assembly within a heater coil and compression monitor set at a predetermined current and time;

cycling said assembly through a heating time, compression time and cooling time; and removing said glass capillary tube and said teflon tube.

6. A method of joining different types of tubes, said method comprising;
 a) providing a first shaft with at least two lumens, wherein said at least two lumens are in a side-by-side arrangement;
 b) providing a second shaft comprised of at least two tube members, wherein each tube member has a lumen associated therewith, and wherein said at least two tube members are arranged in a coaxial arrangement;
 c) inserting at least two mandrils through the entire length of an open lumen of said first shaft such that a portion of said mandrils extends beyond each end of said first shaft;
 d) slidingly engaging one tube member of said second shaft over said mandrils such that a portion of said mandrils extends beyond each end of said tube member;
 e) threading said tube member over said mandrils and inserting a proximal end of said tube member into a distal end of said lumen of said first shaft through which said mandrils have been inserted;
 f) repeating said steps c, d, and e, until only one tube member remains for said second shaft and only one open lumen remains for said first shaft;
 g) slidingly engaging the one remaining tube member over all said mandrils and all previously engaged tube members;
 h) threading said remaining tube member over said mandrils and said tube members and slidingly engaging said remaining tube member over the distal end of said first shaft to create a lap joint; and
 treating said lap joint to seal said first shaft to said second shaft.

* * * * *